United States Patent [19]
Lutz et al.

[11] Patent Number: 5,466,840
[45] Date of Patent: Nov. 14, 1995

[54] PROCESS FOR PREPARING PURIFIED ALKALI METAL SALTS OF 4-SULFOPHENYL-[(1-OXYALKANOYL) AMINO]ALKANOATE WITHOUT ISOLATION OF INTERMEDIATES

[75] Inventors: Gary P. Lutz; George C. Zima; Rex Bernard, all of Kingsport, Tenn.

[73] Assignee: Eastman Chemical Company, Kingsport, Tenn.

[21] Appl. No.: 294,236

[22] Filed: Aug. 22, 1994

[51] Int. Cl.⁶ .................................................. C07C 231/00
[52] U.S. Cl. ................... 554/70; 560/41; 560/142; 554/36; 554/68
[58] Field of Search ...................... 560/142, 41, 173; 554/36, 68, 70

[56] References Cited

U.S. PATENT DOCUMENTS

| | | | |
|---|---|---|---|
| 4,883,612 | 11/1989 | Moyne et al. | 260/402 |
| 4,985,180 | 1/1991 | Bellis et al. | 260/404 |

FOREIGN PATENT DOCUMENTS

| | | | |
|---|---|---|---|
| 0105672A1 | 4/1984 | European Pat. Off. | |
| 0355384 | 7/1989 | European Pat. Off. | C07C 309/42 |
| 0355384A1 | 2/1990 | European Pat. Off. | |

*Primary Examiner*—José G. Dees
*Assistant Examiner*—Rosalynd A. Williams
*Attorney, Agent, or Firm*—Betty J. Boshears; Harry J. Gwinnell

[57] ABSTRACT

This invention relates to a 5 step process for preparing a purified alkali metal salt of 4-sulfophenyl-[(1-oxyalkanoyl)amino]alkanoate in one reaction vessel without isolation of intermediates. The steps are as follows: A) reacting an alkali metal salt of 4-hydroxybenzenesulfonic acid with a $C_2$ to $C_4$ carboxylic anhydride in a solvent to form an alkali metal salt of 4-acyloxybenzenesulfonic acid and a $C_2$ to $C_4$ carboxylic acid. B) adding an [(1-oxyalkanoyl)amino]alkanoic acid and a transesterification catalyst to the reaction product of step A) and heating at a temperature and pressure sufficient to maintain reflux of the solvent and to remove the $C_2$ to $C_4$ carboxylic acid from the reaction vessel to form a reaction mixture containing an alkali metal salt of 4-sulfophenyl-[(1-oxyalkanoyl)amino]alkanoate. C) removing the solvent from the reaction mixture formed in step B). D) mixing the alkali metal salt of 4-sulfophenyl-[(1-oxyalkanoyl)amino]alkanoate product of step C) with acetic acid. E) and finally separating the product from the acetic acid. The purified alkali metal salt of 4-sulfophenyl-[(1-oxyalkanoyl)amino]alkanoate product is useful as a bleach activator in detergents.

21 Claims, No Drawings

PROCESS FOR PREPARING PURIFIED ALKALI METAL SALTS OF 4-SULFOPHENYL-[(1-OXYALKANOYL) AMINO]ALKANOATE WITHOUT ISOLATION OF INTERMEDIATES

FIELD OF THE INVENTION

This invention relates to a five step process for preparing a purified alkali metal salt of 4-sulfophenyl-[(1-oxyalkanoyl)amino]alkanoate.

BACKGROUND OF THE INVENTION

Acyloxybenzenesulfonic acid salts are used as bleach activators in detergents. European Patent Application No. 0 355 384 A1 discloses a procedure for preparing 4-acyloxybenzenesulfonic acid salts by reacting 4-hydroxybenzenesulfonic acid salts with an anhydride and a carboxylic acid. An acyloxybenzenesulfonic acid salt is isolated from the reaction mixture. After termination of the reaction, the acyloxybenzenesulfonic acid salt is washed with a hydrophilic solvent such as an alcohol. Such a procedure should not be used to prepare an alkali metal salt of 4-sulfophenyl-[(1-oxyalkanoyl)amino]alkanoate because the intermediate [(1-oxyalkanoyl)amino]alkanoic acid can cyclize to form an acyl lactam which is not useful as a bleach activator and must be removed from the product. Additional purification steps would also reduce the yield of the product.

European Patent Application No. 0 105 672 A1 discloses a one-pot method of preparing an acyloxybenzene sulphonate salt wherein sodium 4-hydroxybenzenesulfonate reacts simultaneously with acetic anhydride and a carboxylic acid. The separation and recycling of the excess carboxylic acid is accomplished by washing with a hydrophobic solvent such as ether or hexane. A disadvantage of this procedure is that the intermediate, sodium 4-hydroxybenzenesulfonate, is insoluble in the hydrophobic solvents, and therefore, remains in the product when the reaction is incomplete. An acyloxybenzene sulphonate salt prepared according to European Patent Application No. 0 105 672 A1 does not satisfy the requirements of high-percent-yield and high purity. A further disadvantage is that the sodium 4-hydroxybenzenesulfonate has to be finely ground which is a tedious and cost-intensive process in order to achieve a complete reaction to give the acyloxybenzene sulphonate salt. Otherwise, a part of the intermediate product, 4-hydroxybenzenesulfonate, remains in the final product. Moreover, hydrophobic solvents such as ether or hexane should not be used to purify crude preparations of an alkali metal salt of 4-sulfophenyl-[(1-oxyalkanoyl)amino]alkanoate because the intermediate [(1-oxyalkanoyl)amino]alkanoic acid is not soluble in hydrophobic solvents, and thus, would remain in the product.

Accordingly what is needed is a process to prepare high yields of a purified alkali metal salt of 4-sulfophenyl-[(1-oxyalkanoyl)amino]alkanoate in one reaction vessel without isolation of intermediates. Moreover, the intermediate products such as sodium 4-acetoxybenzenesulfonate and [(1-oxyalkanoyl)amino]alkanoic acid should not remain in the final product. In addition, it would be advantageous to accomplish isolation of the product by direct evaporation of reaction solvent.

SUMMARY OF THE INVENTION

The present invention is directed to a process for preparing a purified alkali metal salt of 4-sulfophenyl-[(1-oxyalkanoyl)amino]alkanoate in one vessel without isolation of intermediates comprising the steps of:

(A) reacting an alkali metal salt of 4-hydroxybenzenesulfonic acid with a $C_2$ to $C_4$ carboxylic anhydride at a sufficient temperature and time in a solvent to form a alkali metal salt of 4-acyloxybenzenesulfonic acid and a $C_2$ to $C_4$ carboxylic acid, wherein the alkali metal salt of 4-hydroxybenzenesulfonic acid and $C_2$ to $C_4$ carboxylic anhydride are present in a mole ratio of 1:1 to 1:40, respectively, and the solvent is present in a weight ratio of 2:1 to 50:1 based on the weight of the alkali metal salt of 4-hydroxybenzenesulfonic acid;

(B) adding an [(1-oxyalkanoyl)amino]alkanoic acid and at least one transesterification catalyst to the reaction product of Step (A) and heating at a temperature of 150° C. to 250° C. for 0.5 to 10 hours and pressure sufficient to maintain reflux of the solvent and to remove the $C_2$ to $C_4$ carboxylic acid from the reaction vessel, to form a reaction mixture containing an alkali metal salt of 4-sulfophenyl-[(1-oxyalkanoyl)amino]alkanoate, wherein the moles of the [(1-oxyalkanoyl)amino]alkanoic acid added is 0.7 to 5 times the moles of the alkali metal salt of 4-hydroxybenzenesulfonic acid used in Step (A);

(C) removing solvent from the reaction mixture containing the alkali metal salt of 4-sulfophenyl-[(1-oxyalkanoyl)amino]alkanoate formed in Step (B);

(D) mixing the alkali metal salt of 4-sulfophenyl-[(1-oxyalkanoyl)amino]alkanoate product of Step (C) with acetic acid; and (E) separating the alkali metal salt of 4-sulfophenyl-[(1-oxyalkanoyl)amino]alkanoate of Step (D) from the acetic acid to obtain a purified alkali metal salt of 4-sulfophenyl-[(1-oxyalkanoyl)amino]alkanoate and an acetic acid filtrate, said purified alkali metal salt of 4-sulfophenyl-[(1-oxyalkanoyl)amino]alkanoate has the general formula:

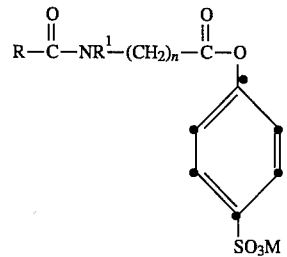

wherein R is selected from the group consisting of $C_5$-$C_{21}$ alkyl, $C_5$-$C_{21}$ alkenyl, chlorinated $C_5$-$C_{21}$ alkyl, and phenyl; $R^1$ is selected from the group consisting of hydrogen and a $C_1$-$C_3$ alkyl; M is selected from the group consisting of hydrogen, ammonium, and an alkali metal atom; and n is an integer from 1 to 8.

DESCRIPTION OF THE INVENTION

The process of the present invention for preparing purified alkali metal salt of 4-sulfophenyl-[(1-oxyalkanoyl)amino] alkanoate involves five steps. In the first step, Step (A), an alkali metal salt of 4-hydroxybenzenesulfonic acid is reacted with a $C_2$ to $C_4$ carboxylic anhydride preferably at a temperature of 100° C. to 250° C. for 0.5 to 5 hours in a solvent to form a alkali metal salt of 4-acyloxybenzenesulfonic acid and a $C_2$ to $C_4$ carboxylic acid. Preferably, the reaction is conducted at a temperature of 140° C. to 170° C. for 1 to 2 hours. Temperatures above 250° C. are not recommended since desulfonation reactions forming a phenol ester instead of a sulfonate are more likely to occur. Preferably, the temperature is maintained below 200° C. The alkali metal salt of the 4-hydroxybenzenesulfonic acid may be any alkali metal salt such as sodium, potassium, calcium, or magnesium. However, sodium is the preferred alkali metal salt.

The $C_2$ to $C_4$ carboxylic anhydride is present in an amount of 1 to 40 moles per mole of the alkali metal salt of 4-hydroxybenzenesulfonic acid, preferably 1 to 5 moles. Most preferably, the $C_2$ to $C_4$ carboxylic anhydride is present in an amount of 1 to 1.5 moles per mole of the alkali metal salt of 4-hydroxybenzenesulfonic acid. Examples of suitable $C_2$ to $C_4$ carboxylic anhydrides are: acetic anhydride, propionic anhydride, butyric anhydride, and isobutyric anhydride. Preferably, the $C_2$ to $C_4$ carboxylic anhydride is acetic anhydride.

Solvents for use in Step (A) include polar aprotic solvents such as N,N-dimethylacetamide; dialkyl sulfoxide wherein the alkyl group has one to six carbon atoms such as dimethyl sulfoxide; dimethyl ethers of diethylene glycol such as triglyme; cyclic or acyclic alkyl sulfones wherein the alkyl group has one to six carbon atoms such as tetrahydrothiophene-1,1-dioxide; and halogenated aromatic solvents such as dichlorobenzene and trichlorobenzene; and alkyl substituted aromatic solvents where the alkyl groups contain one to six carbon atoms such as triisopropylbenzene. Preferably, the solvent is tetrahydrothiophene-1,1-dioxide.

The solvent is present in an amount of 2:1 to 50:1 weight ratio based on the weight of the alkali metal salt of 4-hydroxybenzenesulfonic acid, preferably 4:1 to 6:1 weight ratio. Insufficient solvent results in incomplete solubility of the starting materials which leads to an incomplete reaction and results in longer reaction times and thick pasty reaction mixtures which are difficult to process. Although there is no critical higher limit to the amount of solvent, the use of greater than 50 times the weight of the alkali metal salt of 4-hydroxybenzenesulfonic acid renders the process unnecessarily expensive from the point of view of applying energy for heating and cooling during removal of excess solvent.

Solvents not useful in the process of the present invention include protic solvents such as water, alcohols, and carboxylic acids containing 1 to 20 carbon atoms such as acetic acid. Protic solvents such as alcohols react with the $C_2$ to $C_4$ carboxylic anhydride used in Step (A) and interfere with the transesterification reaction in Step (B). Carboxylic acids such as acetic acid may be used in Step (A), but must be removed in Step (B) to allow the reaction to proceed to completion.

The second step, Step (B), is a transesterification step and involves adding an [(1-oxyalkanoyl)amino]alkanoic acid and a transesterification catalyst to the reaction product of Step (A) and heating at a temperature of 150° C. to 250° C. for 0.5 to 10 hours and pressure sufficient to maintain reflux of the solvent and to remove the $C_2$ to $C_4$ carboxylic acid from the reaction vessel, to form a reaction mixture containing an alkali metal salt of 4-sulfophenyl-[(1-oxyalkanoyl)amino]alkanoate. Preferably, the transesterification reaction is conducted at a temperature of 160° C. to 180° C. for 2 to 6 hours. Removal of the co-product carboxylic acid can be achieved via distillation or by sparging with an inert gas such as nitrogen. Additional solvent may be added in Step (B) to maintain a fluid reaction mixture provided it is the same solvent as used in Step (A). The moles of [(1-oxyalkanoyl)amino]alkanoic acid added is 0.7 to 5 times the moles of the alkali metal salt of 4-hydroxybenzenesulfonic acid used in Step (A).

The [(1-oxyalkanoyl)amino]alkanoic acid is prepared by amidation reactions known in the art which involve reacting a nitrogen containing compound selected from a lactam and an amino acid with a carboxylic acid or ester. Preferably, the [(1-oxyalkanoyl)amino]alkanoic acid is 6-[(1-oxyoctyl)amino]hexanoic acid, 6-[(1oxynonyl)amino]hexanoic acid or 6-[(1-oxydecyl)amino]hexanoic acid. Mixtures of [(1-oxyalkanoyl)amino]alkanoic acids may also be used.

Suitable lactam monomers contain at least 3 carbon atoms per molecule, preferably 4 to 7 carbon atoms per molecule. Suitable lactam monomers include butyrolactam, valerolactam, epsilon-caprolactam, beta-propiolactam, delta-valerolactam, and similar lactams. These lactams may be substituted at the nitrogen atom by hydrocarbon radicals containing one to three carbon atoms. For example, methylcaprolactam may be used. Epsilon-caprolactam and substituted derivatives thereof are the preferred lactam monomers.

The amino acid has the general formula $NH_2(CR'R'')_m COOH$ and is characterized by a basic amino group ($NH_2$) and an acidic carboxyl group (COOH). The letter m in the formula is 1–26, preferably 1–10. The R' and R'' groups are independently selected from hydrogen, unsubstituted or substituted straight chain or branched $C_1$-$C_{20}$ alkyl, unsubstituted or substituted $C_3$-$C_8$ cycloalkyl, $C_3$-$C_8$ alkenyl, $C_3$-$C_8$ alkynyl, and $C_6$-$C_{14}$ aryl.

The unsubstituted and substituted $C_3$-$C_8$ cycloalkyl groups mentioned above refer to cycloaliphatic hydrocarbon groups which contain 3 to 8 carbons in the ring, preferably 5 or 6 carbons, and these cycloalkyl groups substituted with one or two of $C_1$-$C_4$ alkyl, $C_1$-$C_4$ alkoxy, hydroxy or $C_1$-$C_4$ alkanoyloxy.

The $C_3$-$C_8$ alkenyl and $C_3$-$C_8$ alkynyl groups represent straight or branched chain hydrocarbon radicals containing 3 to 8 carbons in the chain and which contain a carbon-carbon double bond or a carbon-carbon triple bond, respectively.

The term "aryl" is used to include carbocyclic aryl groups containing up to fourteen carbons, e.g., phenyl and naphthyl, and those substituted with one or two groups selected from $C_1$-$C_4$-alkyl, $C_1$-$C_4$ alkoxy, $C_1$-$C_4$-alkoxycarbonyl, $C_1$-$C_4$-alkanoyloxy, $C_1$-$C_4$-alkanoylamino, halogen, cyano, $C_1$-$C_4$-alkylsulfonyl, $C_1$-$C_4$-alkylene-$(OH)_n$, O-$C_1$-$C_4$-alkylene-$(OH)_n$, -S-$C_1$-$C_4$-alkylene-$(OH)_n$, -$SO_2$-$C_1$-$C_4$-alkylene-$(OH)_n$, -$CO_2$-$C_1$-$C_4$-alkylene-$(OH)_n$, $SO_2N$ $(R_{17})C_1$-$C_4$-alkylene-$(OH)_n$, -$SO_2N(C_1$-$C_4$-alkylene-$OH)_2$, -$CON(R_{17})C_1$-$C_4$-alkylene-$(OH)_n$, -$CON(C_1$-$C_4$-alkylene-$OH)_2$, -N( $SO_2C_1$-$C_4$-alkyl)-alkylene-$(OH)_n$ or -N($SO_2$ phenyl)-$C_1$-$C_4$-alkylene-$(OH)_n$; wherein n is one or two.

The term "aryl" is also used to include heterocyclic aryl groups such as a 5 or 6-membered heterocyclic aromatic ring containing one oxygen atom, and/or one sulfur atom, and/or up to three nitrogen atoms, said heterocyclic aryl ring optionally fused to one or two phenyl rings or another 5 or 6-membered heteroaryl ring. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl, and the like and those rings substituted with one or more substituents listed above in the definition of the term "aryl".

In addition, the term "aryl" includes arylene groups. The term "arylene" is used to represent a divalent carbocyclic aryl hydrocarbon moiety containing up to fourteen carbons, e.g., o-, m- and p-phenylene, and those substituted with one or two groups selected from $C_1$-$C_4$-alkyl, $C_1$-$C_4$-alkoxy or halogen.

The carboxylic acid compound is a carboxylic acid or carboxylic acid ester, or combination thereof, which contains an aliphatic, such as a straight or branched chain, or aliphatic radical, cycloaliphatic or hydroaromatic radical. The carboxylic acid or carboxylic acid ester has 6–26 carbon atoms, preferably 8–20 carbon atoms, and most preferably 8–10 carbon atoms. These radicals may be connected to the carboxyl group through an aromatic radical. The carboxylic acids and carboxylic acid esters may be straight or branched chain fatty acids of natural or synthetic origin which may be of a saturated or unsaturated nature. The carboxylic acids and esters can contain more than one carboxylic acid or ester group. Esters of carboxylic acids include, but are not limited to, the methyl, ethyl, propyl, and butyl ester of a carboxylic acid. The carboxylic acids and carboxylic acid esters may be used in pure form or else in the form of their mixtures as commercially available.

Examples of carboxylic acids and carboxylic acid esters are: caprylic acid, methyl caprylate, pelargonic acid, methyl pelargonate, capric acid, methyl caprate, isopropyl caprate, undecylic acid, lauric acid, palmitic acid, stearic acid, oleic acid, linoleic acid, behenic acid, terephthalic acid, dimethyl terephthalate, phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like. Preferred carboxylic acids are capric and caprylic. Preferred carboxylic acid esters are methyl caprate and methyl caprylate.

Tranesterification catalysts for use in Step (B) are known to those skilled in the art. Such transesterification catalysts include: tertiary amine catalysts, alkali metal salts, metallic catalysts, acidic catalysts, and combinations thereof. Specific examples of transesterification catalysts for use in the process of the present invention are: dimethyl aminopyridine, imidazole, sodium acetate, sodium hydroxide, and titanium tetraisopropoxide. The transesterification catalyst(s) is added in an amount of 0.01 to 0.3 moles per mole of the alkali metal salt of 4-hydroxybenzenesulfonic acid used in Step (A). More than one transesterification catalyst may be used in Step (B).

A by-product of the transesterification step, Step (B), in the case where 6-[(1-oxyoctyl)amino]hexanoic acid is used as the [(1-oxyalkanoyl)amino]alkanoic acid is hexanoic acid, 6-[[1-oxo-6-[(1-oxooctyl)amino]hexyl]amino]-,4-sulfophenyl ester, mono sodium salt. In the case where 6-[(1-oxynonyl)amino]hexanoic acid is used, a by-product of the transesterification is hexanoic acid, 6-[[1-oxo-6-[(1-oxononyl)amino]hexyl]amino]-, 4-sulfophenyl ester, mono sodium salt. In the case where 6-[(1-oxydecyl)amino]hexanoic acid is used, a by-product of the transesterification is hexanoic acid, 6-[[1-oxo-6-[(1-oxodecyl)amino]hexyl] amino]-, 4-sulfophenyl ester, mono sodium salt. Such impurities have the general formula:

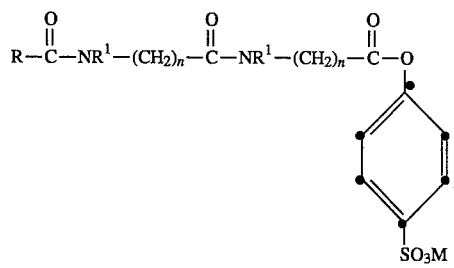

In the above formula, R is a $C_5$-$C_{21}$ alkyl, $C_5$-$C_{21}$ alkenyl, chlorinated $C_5$-$C_{21}$ alkyl, or phenyl that can be substituted by 1 to 3 substituents from among the groups F, Cl, $SO_3M$, COOM, $C_1$-$C_{21}$ alkyl, or $C_2$-$C_{20}$ alkenyl; $R^1$ independently represents hydrogen and a $C_1$-$C_3$ alkyl; M represents hydrogen, ammonium, or an alkali metal atom such as sodium and potassium; and n is an integer from 1 to 8.

The third step, Step (C), involves removing solvent from the reaction mixture containing alkali metal salt of 4-sulfophenyl-[(1-oxyalkanoyl) amino]alkanoate formed in Step (B). Removal of solvent is accomplished either by an evaporative process such as distillation or drying, or by crystallization followed by filtration. Removal of the solvent is conducted at low vacuum and at a temperature which vaporization of the solvent occurs. Preferably, the vacuum range is from 0.5 absolute to 100 mm Hg, and the temperature range is from 140° C. to 250° C. Preferably, at least 90% of the solvent is removed by evaporation. More preferably, at least 95% of the solvent is removed by evaporation. It is important to note that crystallization from the reaction solvent can be problematic as a form of product isolation since solvents tend to complex with the alkali metal salt of 4-sulfophenyl-[(1oxyalkanoyl)amino]alkanoate to produce a gel.

The fourth step, Step (D), involves adding acetic acid to the alkali metal salt of 4-sulfophenyl-[(1-oxyalkanoyl)amino]alkanoate product of Step (C). The acetic acid should contain less than 5% water. Preferably, glacial acetic acid which is >99% pure carboxylic acid is used. $C_1$ to $C_4$ alcohols and acids and their corresponding esters may be used in place of acetic acid in the purification step with a lesser degree of performance. Purification of the alkali metal salt of 4-sulfophenyl-[(1-oxyalkanoyl)amino]alkanoate is accomplished by methods known in the art such as reslurry, wash, digestion and recrystallization.

The acetic acid removes impurities formed during the process such as hexanoic acid, 6-[[1-oxo-6-[(1-oxooctyl)amino]hexyl]amino]-,4-sulfophenyl ester, mono sodium salt, hexanoic acid, 6-[[1-oxo-6-[(1-oxononyl)amino]hexyl] amino]-,4-sulfophenyl ester, mono sodium salt, and hexanoic acid, 6-[[1-oxo-6-[(1-oxodecyl)amino]hexyl]amino]-, 4-sulfophenyl ester, mono sodium salt; residual solvent; and unreacted starting materials, from the reaction product. In addition, the acetic acid reduces color of the alkali metal salt of 4-sulfophenyl-[(1oxyalkanoyl)amino]alkanoate product which is recovered in the form of a solid.

The fifth step, Step (E), involves separating the solid alkali metal salt of 4-sulfophenyl-[(1-oxyalkanoyl)amino] alkanoate product from the acetic acid solution to obtain a purified alkali metal salt of 4-sulfophenyl--[(1-oxyalkanoyl)amino]alkanoate and an acetic acid filtrate. Separation is accomplished by methods known in the art such as centrifugation or vacuum filtration. The filtrate from Step (E) of a previous preparation can be recycled and added as part of the acetic acid to Step (D) to minimize the loss of product. The product is dried by any standard drying technique such as in a ring drier, or a vacuum oven. Step (D) and Step (E) may be repeated until the alkali metal salt of 4-sulfophenyl-[(1-oxyalkanoyl)amino]alkanoate of a desired purity is obtained. Depending on the purity of the [(1-oxyalkanoyl)amino]alkanoic acid starting material, greater than 80% yield of product is obtained by the process of the present invention.

The process of the present invention for preparing purified alkali metal salt of 4-sulfophenyl-[(1-oxyalkanoyl)amino] alkanoate may be conducted stepwise as a batch process or as a continuous process. The purified alkali metal salt of 4-sulfophenyl-[(1-oxyalkanoyl)amino]alkanoate product has the general formula:

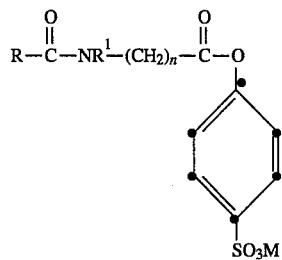

In the above formula, R represents $C_5$-$C_{21}$ alkyl, $C_5$-$C_{21}$ alkenyl, chlorinated $C_5$-$C_{21}$ alkyl, or phenyl that can be substituted by 1 to 3 substituents from among the groups F, Cl, $SO_3M$, COOM, $C_1$-$C_{21}$ alkyl, or $C_2$-$C_{20}$ alkenyl; $R^1$ represents hydrogen or a $C_1$-$C_3$ alkyl; M represents hydrogen, ammonium, or an alkali metal atom such as sodium and potassium; and n is an integer from 1 to 8. Preferably, the purified alkali metal salt of 4-sulfophenyl-[(1-oxyalkanoyl)amino]alkanoate product is sodium 4-sulfophenyl-6-[(1-oxyoctyl)amino]hexanoate wherein R is $C_7H_{15}$, n is 5, and M is sodium; sodium 4-Sulfophenyl-6-[(1-oxynonyl)amino] hexanoate, wherein R is $C_8H_{17}$, n is 5, and M is sodium; or sodium 4-sulfophenyl-6-[(1-oxydecyl)amino]hexanoate wherein R is $C_9H_{19}$, n is 5, and M is sodium. The product may also be a mixture of these compounds.

The materials and testing procedures used for the results shown herein are as follows:

Liquid Chromatography method for determining the purity of the alkali metal salt of 4-sulfophenyl-[(1-oxyalkanoyl)amino]alkanoate product: A weighed amount of sample is diluted and injected onto a reversed-phase liquid chromatographic column using a water/acetonitrile mobile phase containing an ion-pairing reagent. An ultra-violet (UV) detector, set at 205 nm, is used to monitor component elution. The peak areas of the sample components are compared to the peak areas obtained from the injection of known standards to determine the concentration of each component.

The process of the present invention will be further illustrated by a consideration of the following examples, which are intended to be exemplary of the invention. All parts and percentages in the examples are on a weight basis unless otherwise stated.

EXAMPLE 1

A one vessel synthesis of sodium 4-sulfophenyl-6-[(1-oxyoctyl)amino]hexanoate and sodium 4-sulfophenyl-6-[(1-oxydecyl)amino]hexanoate without a purification step.

To 60 grams of tetrahydrothiophene-1,1-dioxide at 140° C. was added with stirring 8.3 grams, 0.042 mole, of sodium 4-hydroxybenzenesulfonate and 6.4 grams, 0.063 mole, of acetic anhydride. The resulting mixture was allowed to stir at 140° C. for 2 hours before the pressure was reduced to 100–160 mm of Hg for 45 minutes. The temperature of the reaction mixture was then increased to 170° C., and 12 grams, approximately 0.046 mole, of a mixture of 6-[(1-oxyoctyl)amino]hexanoic acid and 6-[(1-oxydecyl)amino] hexanoic acid, 0.14 grams, 0.0014 mole, of imidazole, and 0.17 grams, 0.0020 mole, of sodium acetate was added. The resulting reaction mixture was allowed to stir for approximately 3 hours at 100 mm of Hg with a nitrogen sweep of approximately 0.5 cubic feet per hour. Acetic acid spontaneously evaporated from the reactor throughout the reaction and was not collected. After the three hour reaction time, the pressure was reduced to 20 mm of Hg and tetrahydrothiophene-1,1-dioxide was allowed to distill out of the reactor. After no further tetrahydrothiophene-1,1-dioxide would distill out of the reactor, the reaction mass, approximately 20 grams, was allowed to cool to a hard solid. The hard solid, 16.7 grams, was ground to a sand-like consistency and was placed into a vacuum oven at 70° C. for approximately 70 hours to yield 13.7 grams of dried product. HPLC data on the dried product is summarized in Table I.

EXAMPLE 2

A one vessel synthesis of sodium 4-sulfophenyl-6-[(1-oxyoctyl)amino]hexanoate and sodium 4-sulfophenyl-6-[(1-oxydecyl)amino]hexanoate without a purification step.

To 172 grams of tetrahydrothiophene-1,1-dioxide at approximately 35° C. was added with stirring 29 grams, 0.12 mole, sodium 4-acetoxybenzenesulfonate, 34 grams of a mixture containing 51% of 6-[(1-oxyoctyl)amino]hexanoic acid and 34% of 6-[(1-oxydecyl)amino]hexanoic acid, 0.40 grams, 0.0060 mole, imidazole, and 0.49 grams, 0.0058 mole, sodium acetate. The reaction mixture was allowed to warm to approximately 170° C. as the pressure was reduced to about 20 mm of Hg. [This combination of pressure and temperature provided a steady reflux at the top of a 15" long distillation column packed with 12" of stainless steel packing material.] The reaction mixture was allowed to reflux for approximately 1 hour before the pressure was reduced to allow the solvent to distill out of the reaction flask. The pressure was lowered in stages to about 5 mm of Hg until no further solvent distilled out of the reaction flask (approximately 1.7 hour elapsed during the distillation). The resulting pasty solid was allowed to cool to a hard solid, approximately 90 grams. The hard solid, 84.4 grams, was ground to a sand-like consistency and was placed into a vacuum oven at 130° C. and 29" of Hg for approximately 18 hours to yield 53.6 grams of dried product. HPLC data on the dried product is summarized in Table I.

EXAMPLE 3

A one vessel synthesis of sodium 4-sulfophenyl-6-[(1-oxyoctyl)amino]hexanoate and sodium 4-sulfophenyl-6-[(1-oxydecyl)amino]hexanoate without a purification step.

To 172 grams of tetrahydrothiophene-1,1-dioxide at approximately 35° C. was added with stirring 29 grams, 0.12 mole, sodium 4-acetoxybenzenesulfonate, 34 grams of a mixture containing 51% of 6-[(1-oxyoctyl)amino]hexanoic acid and 34% of 6-[(1-oxydecyl)amino]hexanoic acid, 0.40 grams, 0.0060 mole, imidazole, and 0.49 grams, 0.0058 mole, sodium acetate. The reaction mixture was allowed to warm to approximately 170° C. as the pressure was reduced to about 20 mm of Hg. [This combination of pressure and temperature provided a steady reflux at the top of a 15" long distillation column packed with 12" of stainless steel packing material.] The reaction mixture was allowed to reflux for approximately 1 hour before the pressure was reduced to allow the solvent to distill out of the reaction flask. The pressure was lowered in stages to about 5 mm of Hg until no further solvent distilled out of the reaction flask (approximately 1.7 hour elapsed during the distillation). The resulting pasty solid was allowed to cool to a hard solid, approximately 90 grams. The hard solid, 82.6 grams, was ground to a sand-like consistency and was placed into a vacuum oven at 130° C. and 29" of Hg for approximately 18 hours to yield 53.7 grams of dried product. HPLC data on the dried product is summarized in Table I.

EXAMPLE 4

Purification of the product prepared in Example 3.

dark colored filtrate. The wet solids were allowed to dry in a vacuum oven at 70° C. and 20 inches of Hg for approximately 18 hours to yield 65.8 grams of dried material. HPLC data on the dried material is summarized in Table I.

EXAMPLE 6

To 316.4 grams of filtrate recovered in Example 5 was added 105.6 grams of glacial acetic acid and 105.3 grams of crude reaction product prepared in a manner analogous to that described in Example 2. The resulting mixture was allowed to warm to 70° C. for 20 minutes before being allowed to cool to 25° C. The mixture was filtered to obtain 153.2 grams of acetic acid wet solids and 357.3 grams of dark colored filtrate. The wet solids were allowed to dry in a vacuum oven at 70° and 20 inches of Hg for approximately 18 hours to yield 84.8 grams of dried material. HPLC data on the dried material is summarized in Table I.

TABLE I

| | \multicolumn{10}{c}{HPLC Analysis in Percent By Weight} | | |
|---|---|---|---|---|---|---|---|---|---|---|---|---|
| | PRODUCT | | IMPURITY[1] | | IMPURITY[2] | | STARTING MATERIAL | | IMPURITY[3] | | | |
| Ex. | C-10 | C-8 | C-10 | C-8 | C-10 | C-8 | C-10 | C-8 | C-10 | C-8 | ABS | SPS |
| 1 | 25% | 45% | 5% | 10% | 1% | 0% | 5% | 2% | 1% | 1% | 1% | 6% |
| 2 | 27% | 44% | 5% | 9% | 1% | 1% | 1% | 3% | 0% | 1% | 1% | 5% |
| 3 | 28% | 48% | 5% | 10% | 0% | 0% | 1% | 3% | 1% | 2% | 0% | 5% |
| 4 | 37% | 53% | 1% | 3% | 0% | 0% | 1% | 1% | 0% | 1% | 0% | 2% |
| 5 | 34% | 52% | 2% | 4% | 0% | 0% | 2% | 1% | 0% | 1% | 0% | 3% |
| 6 | 32% | 51% | 3% | 5% | 0% | 0% | 3% | 1% | 0% | 1% | 0% | 3% |

Product (C8) = alkali metal salt of 4-sulfophenyl-6-[(1-oxyoctyl)amino]hexanoate
Product (C10) = alkali metal salt of 4-sulfophenyl-6-[(1-oxydecyl)amino]hexanoate
Impurity[1] (C8) = hexanoic acid, 6-[[1-oxo-6-[(1-oxooctyl)amino]hexyl]amino]-,4-sulfophenyl ester, mono sodium salt
Impurity[2] (C10) = hexanoic acid, 6-[[1-oxo-6-[(1-oxodecyl)amino]hexyl]amino]-,4-sulfophenyl ester, mono sodium salt
Impurity[2] (C8) = sodium 4-octyloxybenzenesulfonate
Impurity[2] (C10) = sodium 4-decyloxybenzenesulfonate
Starting Material (C8) = [(1-oxyoctyl)amino]hexanoic acid
Starting Material (C10) = [(l-oxydecyl)amino]hexanoic acid
Impurity[3] (C8) = 6-[[1-oxo-6-[(1-oxooctyl)amino]hexyl]amino]hexanoic acid
Impurity[3] (C10) = 6-[(1-oxo-6-[(1-oxodecyl)amino]hexyl]amino]hexanoic acid
ABS = sodium 4-acetoxybenzene sulfonate
SPS = sodium 4-hydroxybenzenesulfonate To 215 grams of acetic acid was added with stirring 53.5 grams of crude solid product prepared in Example 3. The resulting mixture was allowed to warm to 70° C. for 20 minutes before being allowed to cool to 25° C. The mixture was filtered to obtain 59.6 grams of acetic acid wet solids and 191.3 grams of dark colored filtrate. The wet solids were allowed to dry in a vacuum oven at 70° C. and 20 inches of Hg for approximately 18 hours to yield 31.1 grams of dried material. HPLC data on the dried product is summarized in Table I.

EXAMPLE 5

Recycle of filtrate recovered in Example 4.

To 189.4 grams of filtrate recovered in Example 4 was added 192.6 grams of glacial acetic acid and 95.0 grams of crude reaction product prepared in a manner analogous to that described in Example 2. The resulting mixture was allowed to warm to 70° C. for 20 minutes before being allowed to cool to 25° C. The mixture was filtered to obtain 139.7 grams of acetic acid wet solids and 319.9 grams of The results in Table I clearly illustrate the effect of the purification step on a sodium 4-sulfophenyl-[(1-oxyalkanoyl)amino]alkanoate product. In Example 4, a 90% pure sodium 4-sulfophenyl-[(1-oxyalkanoyl)amino]alkanoate product was obtained by mixing with acetic acid. The acetic acid removed impurities, residual solvent, and unreacted starting materials from the product. In addition, the results for Examples 1–3 in Table I highlight the reproduceability of the process.

EXAMPLES 7–9

An equal weight of crude reaction product, obtained after Step (B) wherein the reaction solvent had been removed by filtration, and a purification solvent as shown in Table II were combined. The resulting mixture was stirred for 20 minutes at 25° C., filtered, and the solids were dried. HPLC data on the dried material is summarized in Table II.

EXAMPLE 10

A crude reaction product obtained after Step (B) wherein the reaction solvent had been removed by filtration, was combined with acetic acid wherein the amount of acetic acid was 1.7 times the weight of the crude reaction product. The reaction product and acetic acid were heated and mixed for 10 minutes at 70° C., cooled to 25° C. and filtered. The solids were dried. HPLC data on the dried material is summarized in Table II.

TABLE II

| | | Percent of Components Removed During Purification Step | | | |
|---|---|---|---|---|---|
| Ex. | PURIFICATION SOLVENT | PRODUCT | IMPURITY[1] | STARTING MATERIAL | IMPURITY[3] | ABS |
| 7 | Acetic Acid | 1.5% | 34.0% | 77.4% | 58.0% | 47.3% |
| 8 | Methanol | 0% | 4.4% | 77.2% | 47.1% | 54.6% |
| 9 | Methyl Acetate | 0% | 0.0% | 60.9% | 3.4% | 2.9% |
| 10 | Acetic Acid | 7.3% | 93.8% | 83.1% | 100.0% | 94.3% |

Product = sodium salt of 4-sulfophenyl-6-[(1-oxydecyl)amino]hexanoate.
Impurity[1] = hexanoic acid, 6-[[1-oxo-6-[(1-oxodecyl)amino]hexyl]amino]-,4-sulfophenyl ester, mono sodium salt
Starting Material = [(1-oxydecyl)amino]hexanoic acid
Impurity[3] = 6-[[1-oxo-6-[(1-oxodecyl)amino]hexyl]amino]hexanoic acid
ABS = sodium 4-acetoxybenzene sulfonate The results in Table II clearly show that acetic acid removes significantly more impurities, residual solvent, and unreacted starting materials from the alkali metal salt of 4-sulfophenyl-[(1-oxyalkanoyl)amino]alkanoate product than methanol or methyl acetate. Moreover, the acetic acid left the alkali metal salt of 4-sulfophenyl-[(1-oxyalkanoyl)amino]alkanoate product essentially unaffected.

The advantages associated with the process of the present invention are that a purified alkali metal salt of 4-sulfophenyl-[(1-oxyalkanoyl)amino]alkanoate is prepared without isolation of the 4-acetoxybenzenesulfonate. In addition, the purification is accomplished using acetic acid which is unexpected because acetic acid is a by-product in the transesterification reaction and would be expected to cause the reverse reaction. The present inventors have determined that the acetic acid removes impurities, residual solvent, and unreacted starting materials from the alkali metal salt of 4-sulfophenyl-[(1-oxyalkanoyl)amino]alkanoate product. Moreover, the acetic acid reduces the color of the purified product.

In addition, direct evaporation of solvent in Step (C) avoids gel formation which typically occurs upon cooling of the reaction mixture when more than one [(1-oxyalkanoyl)amino]alkanoic acid is used.

Many variations will suggest themselves to those skilled in this art in light of the above detailed description. All such obvious modifications are within the full intended scope of the appended claims.

What is claimed is:

1. A process for preparing a purified alkali metal salt of 4-sulfophenyl-[(1-oxyalkanoyl)amino]alkanoate in one vessel without isolation of intermediates comprising the steps of:

(A) reacting an alkali metal salt of 4-hydroxybenzenesulfonic acid with a $C_2$ to $C_4$ carboxylic anhydride at a sufficient temperature and time in a solvent to form a alkali metal salt of 4-acyloxybenzenesulfonic acid and a $C_2$ to $C_4$ carboxylic acid, wherein the alkali metal salt of 4-hydroxybenzenesulfonic acid and $C_2$ to $C_4$ carboxylic anhydride are present in a mole ratio of 1:1 to 1:40, respectively, and the solvent is present in a weight ratio of 2:1 to 50:1 based on the weight of the alkali metal salt of 4-hydroxybenzenesulfonic acid, provided that excess carboxylic anhydride is removed under reduced pressure from the reaction vessel;

(B) adding an [(1-oxyalkanoyl)amino]alkanoic acid and at least one transesterification catalyst to the reaction product of Step (A) and heating at a temperature of 150° C. to 250° C. for 0.5 to 10 hours and pressure sufficient to maintain reflux of the solvent and to remove the $C_2$ to $C_4$ carboxylic acid from the reaction vessel, to form a reaction mixture containing an alkali metal salt of 4-sulfophenyl-[(1oxyalkanoyl)amino]alkanoate, wherein the moles of the [(1-oxyalkanoyl)amino]alkanoic acid added is 0.7 to 5 times the moles of the alkali metal salt of 4-hydroxybenzenesulfonic acid used in Step (A);

(C) removing solvent from the reaction mixture containing the alkali metal salt of 4-sulfophenyl-[(1oxyalkanoyl)amino]alkanoate formed in Step (B);

(D) mixing the alkali metal salt of 4-sulfophenyl-[(1oxyalkanoyl)amino]alkanoate product of Step (C) with acetic acid; and (E) separating the alkali metal salt of 4-sulfophenyl-[(1-oxyalkanoyl)amino]alkanoate of Step (D) from the acetic acid to obtain a purified alkali metal salt of 4-sulfophenyl-[(1oxyalkanoyl)amino]alkanoate and an acetic acid filtrate, said purified alkali metal salt of 4-sulfophenyl-[(1-oxyalkanoyl)amino]alkanoate has the general formula:

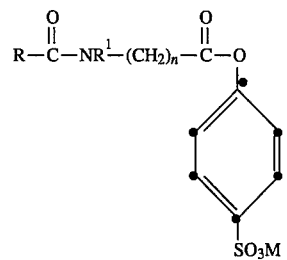

wherein R is selected from the group consisting of $C_5$-$C_{21}$ alkyl, $C_5$-$C_{21}$ alkenyl, chlorinated $C_5$-$C_{21}$ alkyl, and phenyl; $R^1$ is selected from the group consisting of hydrogen and a $C_1$-$C_3$ alkyl; M is selected from the group consisting of hydrogen, ammonium, and an alkali metal atom; and n is an integer from 1 to 8.

2. A process for preparing purified sodium 4-sulfophenyl-6-[(1-oxyoctyl)amino]hexanoate in one vessel without isolation of intermediates comprising the steps of:

(A) reacting sodium 4-hydroxybenzenesulfonate with acetic anhydride at a temperature of 100° C. to 200° C.

for 0.5 to 5 hours in tetrahydrothiophene-1,1-dioxide to form sodium 4-acetoxybenzenesulfonic acid and acetic acid, wherein the sodium 4-hydroxybenzenesulfonate and acetic anhydride are present in a mole ratio of 1:1 to 1:5, respectively, and the tetrahydrothiophene-1,1-dioxide is present in an amount of 2:1 to 50:1 weight ratio based on the weight of the sodium 4-hydroxybenzenesulfonate, provided that excess acetic anhydride is removed under reduced pressure from the reaction vessel;

(B) adding 6-[(1-oxyoctyl)amino]hexanoic acid and at least one transesterification catalyst to the reaction product of Step (A) and heating at a temperature of 150° C. to 250° C. for 0.5 to 10 hours and pressure sufficient to maintain reflux of the tetrahydrothiophene-1,1-dioxide and to remove the acetic acid from the reaction vessel, to form a reaction mixture containing sodium 4-sulfophenyl-6-[(1oxyoctyl)amino]hexanoate, wherein the moles of the 6-[(1-oxyoctyl)amino]hexanoic acid added is 0.7 to 5 times the moles of the sodium 4-hydroxybenzenesulfonate used in Step (A);

(C) evaporating tetrahydrothiophene-1,1-dioxide from the reaction mixture containing the sodium 4-sulfophenyl-6-[(1-oxyoctyl)amino]hexanoate formed in Step (B);

(D) mixing the sodium 4-sulfophenyl-6-[(1-oxyoctyl)amino]hexanoate product of Step (C) with acetic acid; and (E) separating the sodium 4-sulfophenyl-6-[(1-oxyoctyl)amino]hexanoate of Step (D) from the acetic acid.

3. A process for preparing purified sodium 4-sulfophenyl-6-[(1-oxynonyl)amino]hexanoate in one vessel without isolation of intermediates comprising the steps of:

(A) reacting sodium 4-hydroxybenzenesulfonate with acetic anhydride at a temperature of 100° C. to 200° C. for 0.5 to 5 hours in tetrahydrothiophene-1,1-dioxide to form sodium 4-acetoxybenzenesulfonic acid and acetic acid, wherein the sodium 4-hydroxybenzenesulfonate and acetic anhydride are present in a mole ratio of 1:1 to 1:5, respectively, and the tetrahydrothiophene-1,1-dioxide is present in an amount of 2:1 to 50:1 weight ratio based on the weight of the sodium 4-hydroxybenzenesulfonate, provided that excess acetic anhydride is removed under reduced pressure from the reaction vessel;

(B) adding 6-[(1-oxynonyl)amino]hexanoic acid and at least one transesterification catalyst to the reaction product of Step (A) and heating at a temperature of 150° C. to 250° C. for 1 to 6 hours and pressure sufficient to maintain reflux of the tetrahydrothiophene-1,1-dioxide and to remove the acetic acid from the reaction vessel, to form a reaction mixture containing sodium 4-sulfophenyl-6-[(1oxynonyl)amino]hexanoate, wherein the moles of the 6-[(1-oxynonyl)amino]hexanoic acid added is 0.7 to 5 times the moles of the sodium 4-hydroxybenzenesulfonate used in Step (A);

(C) evaporating tetrahydrothiophene-1,1-dioxide from the reaction mixture containing the sodium 4-sulfophenyl-6-[(1-oxynonyl)amino]hexanoate formed in Step (B);

(D) mixing the sodium 4-sulfophenyl--6--[(1-oxynonyl)amino]hexanoate product of Step (C) with acetic acid; and (E) separating the sodium 4-sulfophenyl-6-[(1-oxynonyl)amino]hexanoate of Step (D) from the acetic acid.

4. A process for preparing purified sodium 4-sulfophenyl-6-[(1-oxydecyl)amino]hexanoate in one vessel without isolation of intermediates comprising the steps of:

(A) reacting sodium 4-hydroxybenzenesulfonate with acetic anhydride at a temperature of 100° C. to 200° C. for 0.5 to 5 hours in tetrahydrothiophene-1,1-dioxide to form sodium 4-acetoxybenzenesulfonic acid and acetic acid, wherein the sodium 4-hydroxybenzenesulfonate and acetic anhydride are present in a mole ratio of 1:1 to 1:5, respectively, and the tetrahydrothiophene-1,1-dioxide is present in an amount of 2:1 to 50:1 weight ratio based on the weight of the sodium 4-hydroxybenzenesulfonate, provided that excess acetic anhydride is removed under reduced pressure from the reaction vessel;

(B) adding 6-[(1-oxydecyl)amino]hexanoic acid and at least one transesterification catalyst to the reaction product of Step (A) and heating at a temperature of 150° C. to 250° C. for 1 to 6 hours and pressure sufficient to maintain reflux of the tetrahydrothiophene-1,1-dioxide and to remove the acetic acid from the reaction vessel, to form a reaction mixture containing sodium 4-sulfophenyl-6-[(1oxydecyl)amino]hexanoate, wherein the moles of the 6-[(1-oxydecyl)amino]hexanoic acid added is 0.7 to 5 times the moles of the sodium 4-hydroxybenzenesulfonate used in Step (A);

(C) evaporating tetrahydrothiophene-1,1-dioxide from the reaction mixture containing the sodium 4-sulfophenyl-6-[(1-oxydecyl)amino]hexanoate formed in Step (B);

(D) mixing the sodium 4-sulfophenyl-6-[(1oxydecyl)amino]hexanoate product of Step (C) with acetic acid; and (E) separating the sodium 4-sulfophenyl-6-[(1-oxydecyl)amino]hexanoate of Step (D) from the acetic acid.

5. The process of claim 1 wherein Step (A) is conducted at a temperature of 140° C. to 170° C. for 1 to 2 hours.

6. The process of claim 1 wherein the carboxylic anhydride in Step (A) is present in an amount of 1 to 5 moles per mole of the alkali metal salt of 4-hydroxybenzenesulfonic acid.

7. The process of claim 1 wherein the carboxylic anhydride is present in an amount of 1 to 1.5 moles per mole of the alkali metal salt of 4-hydroxybenzenesulfonic acid.

8. The process of claim 1 wherein the carboxylic anhydride in Step (A) is selected from the group consisting of acetic anhydride, propionic anhydride, butyric anhydride, and isobutyric anhydride.

9. The process of claim 1 wherein the solvent is selected from the group consisting of polar aprotic solvents, dialkyl sulfoxide wherein the alkyl group has one to six carbon atoms, dimethyl ethers of diethylene glycol, cyclic or acyclic alkyl sulfone wherein the alkyl group has one to six carbon atoms, halogenated aromatic solvents, and alkyl substituted aromatic solvents where the alkyl groups contain one to six carbon atoms.

10. The process of claim 9 wherein the solvent is selected from the group consisting of N,N-dimethylacetamide, dimethyl sulfoxide, triglyme, tetrahydrothiophene-1,1-dioxide, dichlorobenzene, trichlorobenzene, and triisopropylbenzene.

11. The process of claim 10 wherein the solvent is tetrahydrothiophene-1,1-dioxide.

12. The process of claim 1 wherein the solvent in Step (A) is present in an amount of 4:1 to 6:1 weight ratio based on the weight of the alkali metal salt of 4-hydroxybenzenesulfonic acid.

13. The process of claim 1 wherein Step (B) is conducted at a temperature of 160° C. to 180° C. for 2 to 4 hours.

14. The process of claim 1 wherein the transesterification catalyst in Step (B) is selected from the group consisting of tertiary amine catalysts, alkali metal salts, metallic catalysts, and combinations thereof.

15. The process of claim 14 wherein the transesterification catalyst in Step (B) is selected from the group consisting of dimethyl aminopyridine, imidazole, sodium acetate, sodium hydroxide, and titanium tetraisopropoxide.

16. The process of claim 1 wherein the transesterification catalyst in Step (B) is added in an amount of 0.01 to 0.3 moles per mole of the alkali metal salt of 4-hydroxybenzenesulfonic acid used in Step (A).

17. The process of claim 1 wherein the solvent in Step (C) is removed by evaporation at vacuum of 0.5 absolute to 100 mm Hg, and at a temperature of 140° C. to 250° C.

18. The process of claim 1 wherein at least 90% of the solvent is removed in Step (C).

19. The process of claim 18 wherein at least 95% of the solvent is removed in Step (C).

20. The process of claim 1 wherein the acetic acid used in Step (D) is glacial acetic acid.

21. The process of claim 1 wherein the alkali metal salt of 4-sulfophenyl-[(1-oxyalkanoyl)amino]alkanoate product is separated from the acetic acid solution in Step (E) by a method selected from the group consisting of centrifugation and vacuum filtration.

* * * * *

UNITED STATES PATENT AND TRADEMARK OFFICE
CERTIFICATE OF CORRECTION

PATENT NO. : 5,466,840
DATED : November 14, 1995
INVENTOR(S) : Gary P. Lutz et al.

It is certified that error appears in the above-indentified patent and that said Letters Patent is hereby corrected as shown below:

ON THE TITLE PAGE:

Please delete "Betty J. Boshears" as Attorney of Record and insert therefor — John D. Thallemer —. Harry J. Gwinnell's name is to remain.

Signed and Sealed this

Twentieth Day of February, 1996

Attest:

BRUCE LEHMAN

Attesting Officer     Commissioner of Patents and Trademarks